United States Patent [19]

Limousin et al.

[11] Patent Number: 5,312,451
[45] Date of Patent: May 17, 1994

[54] APPARATUS AND METHODS FOR CONTROLLING A CARDIAC PACEMAKER IN THE EVENT OF A VENTRICULAR EXTRASYSTOLE

[75] Inventors: Marcel Limousin, Montrouge; Remy Nitzsche, Beynes; Nicolas Rosset, Montrouge, all of

[73] Assignee: ELA Medical, Montrouge, France

[21] Appl. No.: 997,080

[22] Filed: Dec. 29, 1992

[51] Int. Cl.⁵ .................................. A61N 1/362
[52] U.S. Cl. ............................... 607/15; 607/9
[58] Field of Search ......................... 607/9, 14, 15

[56] References Cited

U.S. PATENT DOCUMENTS

| | | | |
|---|---|---|---|
| 4,284,082 | 8/1981 | Funke et al. | 607/9 |
| 4,452,248 | 6/1984 | Keller, Jr. | 607/27 |

FOREIGN PATENT DOCUMENTS

| | | | |
|---|---|---|---|
| 0241102 | 10/1987 | European Pat. Off. | A61N 1/368 |
| 0436517 | 10/1991 | European Pat. Off. | A61N 1/368 |
| 2544989 | 11/1984 | France | A61N 1/36 |
| 221372 | 4/1985 | German Democratic Rep. | A61N 1/36 |
| 8301389 | 4/1983 | World Int. Prop. O. | A61N 1/36 |

*Primary Examiner*—William E. Kamm
*Assistant Examiner*—Kennedy J. Schaetzle
*Attorney, Agent, or Firm*—Davis Hoxie Faithfull & Hapgood

[57] ABSTRACT

Upon detection of a ventricular extrasystole, a pacing control algorithm is brought into play to trigger: a stimulation of the atrium, a controlling of the atrium at a faster pacing rate than that of the ventricle during some cycles, a synchronous controlling of the ventricle during a period that is a multiple of a programmed number of cycles, and subsequent to the programmed number of cycles, a slowing of the ventricular rate until either the programmed base rate is reached or a further sinus detection occurs. The algorithm is inactivated on certain conditions, inhibited on certain conditions, and reactivated on further sensed ventricular extrasystoles.

44 Claims, 3 Drawing Sheets

APPARATUS AND METHODS FOR CONTROLLING A CARDIAC PACEMAKER IN THE EVENT OF A VENTRICULAR EXTRASYSTOLE

FIELD OF THE INVENTION

This invention relates to a method and apparatus for controlling a cardiac pacemaker, more particularly in the event of ventricular extrasystoles ("VES").

BACKGROUND OF THE INVENTION

A VES is a spontaneous depolarization of the ventricle that is not properly triggered by a preceding atrial event and is out of the person's spontaneous or paced heart rhythm.

For persons having a cardiac pacemaker, in the event of detection of a VES, it is desirable to avoid the occurrence of pacemaker mediated tachycardia ("PMT"). PMT occurs when a VES induces a depolarization of the atrium which is sensed by the pacemaker and which, in turn, initiates an established atrioventricular delay interval and induces a stimulation of the ventricle after that interval. This can cause the pacemaker to accelerate improperly the pacing rate.

SUMMARY OF THE INVENTION

It is an object of the present invention to avoid the compensatory pause following a VES which can trigger ventricular tachycardia in certain patients.

It is another object of the invention is to provide a method for controlling a cardiac pacemaker which, upon detection of a VES, enables a return to spontaneous atrio-ventricular conduction, while ensuring a high ventricular rate to improve the patient's hemodynamics.

It is another object of the present invention to provide a cardiac pacemaker and controlling method which tend to avoid the occurrence of PMT after detection of a VES.

Broadly, the present invention provides a cardiac pacemaker and a method for controlling a cardiac pacemaker in the event of ventricular extrasystoles, wherein, upon detection of a ventricular extrasystole, a pacing control algorithm is brought into play to trigger:
- a stimulation of the atrium,
- a controlling of the atrium at a faster pacing rate than that of the ventricle during some cycles,
- a synchronous controlling of the ventricle during a period that is a multiple of a programmed number of cycles, and
- subsequent to each programmed number of cycles, a slowing of the ventricular rate until a basic pacing rate is reached or until a further spontaneous atrial depolarization is detected.

In a preferred embodiment, the stimulation of the atrium is synchronous with the detected ventricular extrasystole VES and the VES serves as primary event for a ventricular escape interval VEI and for a ventriculo-atrial interval VA which is shorter than the VEI interval. The VEI interval is preferably selected as a percentage of the average interval between two successive P waves, included between 50% and 100%, and preferably equal to 87.5%.

During the programmed number of cycles, the VEI interval is maintained constant, and, at each cycle, the VA interval is reduced while the atrio-ventricular delay AVD interval is increased by corresponding durations to comply with the equality: $VEI = VA + AVD$. Subsequent to each programmed number of cycles, the VEI is increased and maintained constant for the next programmed number of cycles. The programmed number of cycles is preferably equal to 20. The programmed number of cycles is preferably counted by a counter that is initialized by the detection of the VES, more preferably a software-based counter.

The aforementioned pacing control algorithm is only brought into play if a percentage of the average interval between two successive P waves ("PPm") exceeds a predetermined duration, wherein the predetermined duration is preferably equal to 500 ms. This corresponds to a high pacing rate limit of 120 beats per minute.

Upon detection of a new "frequent" VES, the ventricular rate is again increased by an acceleration slope, i.e., the VEI interval is reduced. However, if the accelerated ventricular rate has a corresponding ventricular escape interval that is less than 500 ms, then the algorithm is inactivated. After inactivation of the algorithm, the VEI interval is increased by plateaus until the basic period, i.e., the programmed base pacing rate, is reached or a sinus rhythm is recovered. At that time, the pacing control algorithm of the present invention is inhibited and the cardiac pacemaker returns to its regular operating mode.

BRIEF DESCRIPTION OF THE DRAWINGS

Further features and advantages of the invention will be apparent upon consideration of the following detailed description of a preferred embodiment of the invention, taken in conjunction with the accompanying drawings, in which.

DETAILED DESCRIPTION OF THE INVENTION

It is possible to define two types of VES. The type 1 VES corresponds to a ventricular detection that is not preceded by an atrial event within a given time interval included between, e.g., 31 and 300 ms. The type 2 VES corresponds to a ventricular detection, preceded by a paced atrial event within a given time interval included between, e.g., 31 and 300 ms, in the case where the atrio-ventricular delay "AR" interval is lower by more than 31 ms than the atrio-ventricular delay interval of the preceding cycle ("AVD"): $AVD-AR > 31$ ms. In the following description, VES are indifferently the type 1 or type 2 VES.

VES are further classified in one of two groups. A VES is called frequent (or critical) when it is preceded by a given number of synchronous cardiac cycles, where the given number is lower than a programmed number, for instance 10. Otherwise, a VES is called non-frequent.

In the following description, with reference to FIGS. 1-4, the first sensed VES is considered non-frequent VES, and subsequently sensed VES are considered frequent VES.

Figure 1:
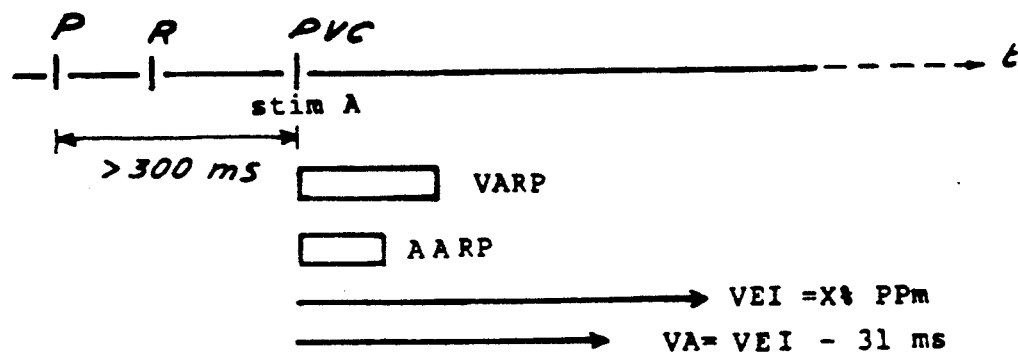
FIG. 1 is a representative diagram of operations triggered upon occurrence of a VES in accordance with an embodiment of the invention.

FIG. 1 illustrates various delays or intervals triggered upon detection of a VES. The VES detection is illustrated by the reference PVC (which also refers to a premature ventricular contraction). The interval PPm is defined as the average interval, preferably over a selected number of cardiac cycles, between two P waves situated outside a post-atrial atrial refractory period ("PAARP") which is triggered by a P wave. The selected number of cardiac cycles is preferably eight. P waves outside the PAARP trigger an atrio-ventricular delay ("AVD") interval. At the end of the AVD interval, the ventricle is stimulated unless a spontaneous depolarization has been detected. Also shown in FIG. 1 are the ventricular absolute refractory period VARP and the atrial absolute refractory period AARP.

Figure 2:
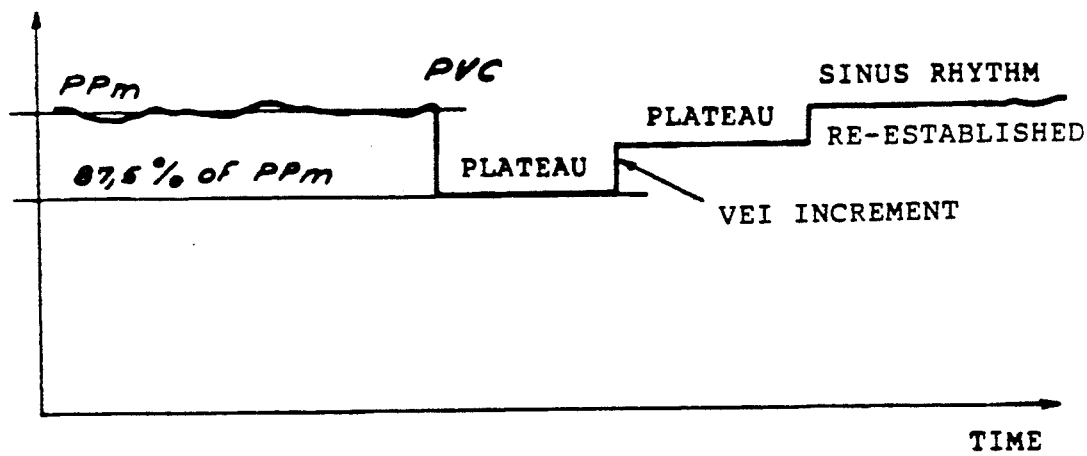
FIG. 2 is a representative graph of the variations of the ventricular interval upon detection of an isolated VES.

FIG. 2 illustrates variations of cardiac rate corresponding to the application of an algorithm brought into play in accordance with the present invention. In this regard, upon detection of a non-frequent VES, the cardiac rate is increased. Preferably, the ventricular escape interval "VEI" is reduced to, for instance, 87.5% of the PPm interval. The reduced interval VEI is then maintained constant for a given time period, referred to as a "plateau." After a plateau, the VEI interval is extended, i.e., increased, by a "VEI increment" slope, and again is maintained constant during a second plateau. After the second plateau, the VEI interval is again extended and maintained constant. This cycle continues until the sinus rhythm is recovered or the basic pacing rate of the patient, which is typically programmed by a doctor, is reached.

Figure 3:
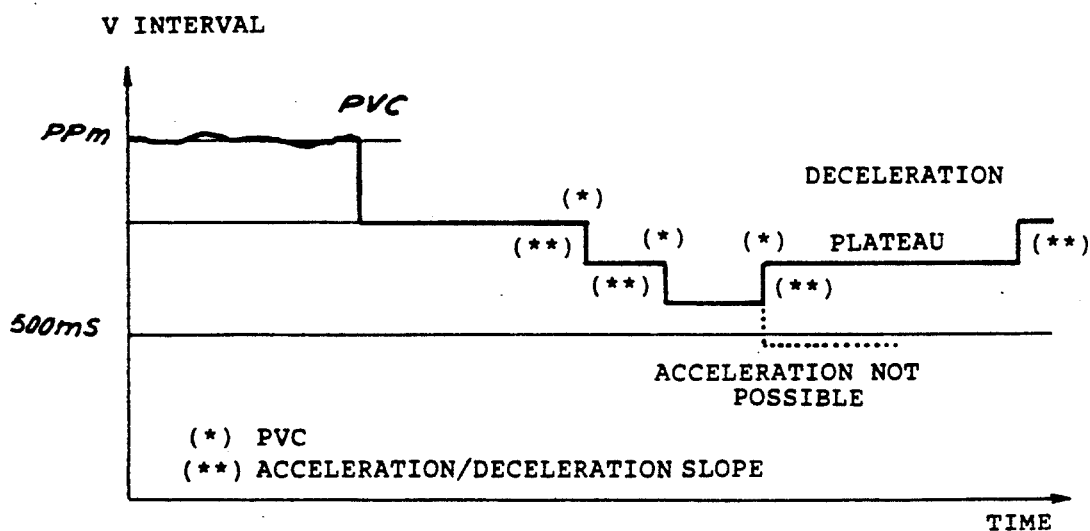
FIG. 3 is a representation of the ventricular interval in the case of proximate VES, leading to the inactivation condition of the algorithm brought into play in the method according to invention.

FIG. 3 illustrates the application of the present invention in the case of a series of sensed VESs, which will be described moving from left to right. Upon detection (sensing) of the first VES, which is identified as non-frequent and designated as a PVC event, the VEI interval is shortened as described. However, before the end of the first plateau, a second VES is sensed, which is determined to be a frequent VES and designated by an "*". This causes the VEI interval to be shortened again. Then, a third VES, also frequent and designed by an "*", is detected and the VEI interval is shortened again. However, upon detection of a fourth VES, which also is frequent and designated by an "*", the VEI interval is not reduced further. This is because, in this illustration, to do so would produce a VEI interval shorter than 500 ms, which corresponds to a pacing rate higher than 120 bpm and is undesired.

Accordingly, in this condition, the pacing control algorithm is inactivated, and the ventricular rate is decreased by plateaus, corresponding to a stepwise increase of the VEI interval by set increments after the end of a selected time interval, as in the case of the example illustrated in FIG. 2. The plateaus are in accordance with a deceleration slope for controlling the rate of change of the pacing rate.

Figure 4:
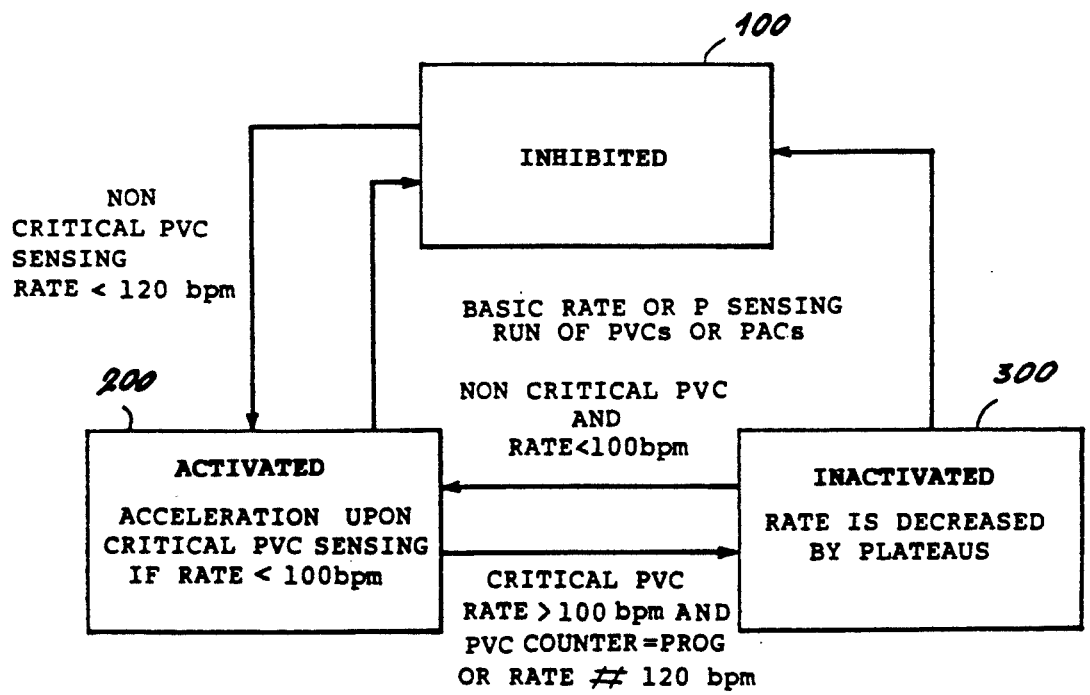
FIG. 4 a flow chart representative of the states of the operation of the control algorithm in accordance with a preferred embodiment of the present invention.

FIG. 4 illustrates a flow chart state diagram of the above described operations in the inhibited state 100, activated state 200, and inactivated state 300 in accordance with the invention. The pacemaker 20 embodying the invention brings the pacer control algorithm into play. Entry to the algorithm is triggered by the detection of a VES, provided that the average cardiac rate is not already too fast. In other words, the algorithm is applied in the activated state 200 if (and until) a proportion of the average interval between two successive P waves, PPm, exceedse a predetermined duration, e.g., 500 ms, wherein the proportion is preferably equal to 87.5%, i.e., PPm×0.875>500 ms.

Entry into state 200 brings about three types of operations. The first operation is the triggering of the several periods illustrated in FIG. 1 in response to a sensed VES designated PVC. These periods are a ventricular absolute refractory period VARP, an atrial absolute refractory period AARP, which is selected to be shorter than the VARP and preferably equal to (VARP−94 ms), a ventricular escape interval VEI which is equal to a percentage X of interval PPm, the percentage being selected from between 50 and 100 and preferably equal to 87.5%, and a ventriculo-atrial delay VA interval which is selected to be shorter than the VEI interval and preferably equal to (VEI−31 ms).

The second operation is a stimulation of the atrium (designated as "stim A" on FIG. 1), if the preceding atrial rate limitation period ARLP triggered by the atrial event is ended. The ARLP is preferably set equal to 400 ms. Every time a P wave is detected outside a post-atrial atrial refractory period PAARP, a new PAARP is triggered having a duration equal either to 75% of the previous interval PP when the interval PP is greater than the PAARP, or to 75% of the average interval PPm in the other case.

The third operation is the initializing of a counter 60, referred to as "same VEI counter", which enables counting of a selected number of ventricular cycles having the same escape interval VEI. The counter is initialized at a number programmed as "same VEI number", e.g., equal to 20, and proceeds by decrements of one to 0.

Subsequent to the detection of a VES and entry into the algorithm, the invention has a threefold objective. The first objective is to ensure faster control of the atrium, or over-driving, i.e., to stimulate the atrium after an increasingly shorter VA delay for a few cycles, while the VEI interval remains constant. The second objective is to attempt to re-establish atrio-ventricular conduction by gradually lengthening the AVD interval. The third objective is to decrease gradually the ventricular rate by gradually lengthening the VEI interval each time the counter 60 returns to the "same VEI number" value, until a sinus detection is recorded (outside the PAARP) or until the basic pacing rate is reached. The basic rate preferably corresponds, e.g., to 60 bpm.

The operation of the algorithm as a function of a sinus detection and a paced atrial event is analyzed as follows. In the absence of sinus detection during the VA interval, the atrium is stimulated at the end of this interval and an atrio-ventricular delay AVD interval of duration AVD=(VEI−VA) is triggered. In the event of sinus detection during the VA interval and outside the PAARP interval, the sinus rhythm is recovered and the algorithm is consequently inhibited at step 100. In the event of sinus detection during the PAARP, this detection corresponds to an atrial extrasystole or AES, and a new VA interval is triggered, with a duration corresponding to the maximum of the following three intervals: PAARP, ARLP and (VEI−31 ms).

The operation of the algorithm as a function of a ventricular event (detection or stimulation) is analyzed as follows. In the absence of ventricular detection during the VEI interval, the ventricle is stimulated at the end of the VEI interval. In order to recover spontaneous atrio-ventricular conduction, the AVD interval is increased. The VEI interval is constant throughout the programmed number of cycles for the counter "same VEI counter 60". Then, and every time the counter corresponds to its programmed "same VEI number" value, the VEI interval is increased by an increment.

Upon ventricular stimulation at the end of the VEI interval, and as long as the programmed number of cycles for the same VEI interval has not been reached (e.g., 20 cycles), the counter 60 "same VEI counter" is decremented by one and the VA interval is decreased according to an "AV delay increment", once per cycle. The "AV delay increment" forms a slope which limits the change in the synchrony from atrial to ventricular event, cycle to cycle. Thus, at each cycle, the AVD interval is increased correlatively, as long as it has not returned to its programmed value.

When the programmed number of cycles for the same VEI interval is reached, the counter 60 value is at 0. The algorithm then re-initializes the counter 60 at the programmed "same VEI number" value, increases the VEI interval according to a "VEI−increment" slope, and modifies the AVD interval to increase it by an "AV delay increment". Thus, the VA interval becomes equal to (VA+"VEI increment"−"AV delay increment"). The AVD interval is then increased as long as spontaneous atrio-ventricular conduction has not been recovered, and as long as the AVD interval has not reached its programmed value.

In the event of synchronous ventricular detection during the VEI interval, spontaneous atrio-ventricular conduction is recovered. It is no longer necessary to increase the AVD interval, but the VEI interval must continue to be gradually increased to reach the basic pacing period or until a sinus detection is recorded.

Upon occurrence of ventricular detection, and as long as the programmed number of cycles for the same VEI interval has not been reached (e.g., 20 cycles), the counter 60 "same VEI counter" is decremented, and the VA and VEI delays are maintained constant.

When the programmed number of cycles for the same VEI is reached, the counter 60 value is at 0. The algorithm then reinitializes the counter at the programmed "same VEI number" value, increases the VEI interval according to a "VEI increment" slope, selected from between 10 and 200 ms, and preferably equal to 60 ms, and modifies the VA interval so as not to modify the AVD interval. In this case, the VA interval becomes equal to (VA+"VEI increment").

The VEI interval remains constant throughout the programmed number of cycles, e.g., 20. The algorithm then triggers a phase identical to the previous one: re-initializing the counter 60, increasing the VEI interval, and modifying the VA interval. This phase is repeated until the VEI interval becomes equal to the basic period of the cardiac pacemaker or there is a sinus detection outside the PAARP, i.e., when the sinus rhythm is recovered.

In the event of detection of a further VES, there are three different outcomes depending on whether this new VES is consecutive to a VES or a non-frequent VES.

If the new VES is non-frequent, the algorithm is activated with the following operations:

a) Triggering of a ventricular absolute refractory period VARP,
b) Triggering of an atrial absolute refractory period AARP shorter than the VARP, and preferably equal to (VARP−94 ms), and
c) re-initializing the counter 60 at the programmed "same VEI number" value.

If the new VES is frequent, but is not consecutive to a VES, the algorithm is applied again, if the VEI interval exceeds (500 ms+"VEI increment"), by increasing the ventricular rate and preserving the AVD interval. The algorithm then triggers: re-initializing the counter 60 at the programmed "same VEI number" value, decreasing the VEI interval by the "VEI increment" value, corresponding with the acceleration slope, and applying a VA interval equal to (VEI−AVD).

If the VEI interval is below (500 ms+"VEI increment"), the situation is analyzed as a failure of the algorithm to prevent VES. The algorithm is consequently inactivated at step 300 (FIG. 4).

If the new VES is consecutive to a VES, the decreasing of the VEI interval is not applied as it would risk triggering ventricular tachycardia by prematurely stimulating a burst of VES. A VES doublet therefore commands an inhibition of the algorithm at step 100 as long as the burst of VES is not ended.

Referring to the state diagram illustrated in FIG. 4, the algorithm is inhibited at state 100 in the following cases:

(1) upon atrial detection outside the PAARP, as the sinus rhythm is recovered;
(2) upon two consecutive atrial extrasystoles AES in a same PAARP, as the atrial rhythm may have been disturbed and a back-up procedure must be activated;
(3) upon ventricular detection or ventricular stimulation when the VEI interval has reached its basic period (corresponding to the basic rate, e.g., an interval of 1000 ms corresponding to a rate of 60 bpm); and
(4) upon two consecutive VES, which can correspond to the triggering of a burst of VES, with inhibition of the algorithm until a non-extrasystolic ventricular event occurs.

In the event of inhibition of the algorithm, the VEI interval is preset at the value of the smoothed VEI interval, and the AVD interval is preset at the value of the programmed AVD interval. The process for smoothing the VEI interval is described in the copending and commonly assigned U.S. patent application Ser. No. 796,003 filed Nov. 22, 1991, which is incorporated by reference herein in its entirety.

According to the present invention, a VES counter 60 is provided, with a value included between 0 and a programmed value, e.g., 50. This VES counter is reset to zero when the algorithm becomes activated at state 200 (FIG. 4). The VES counter 60 is incremented one count upon each detection of a frequent VES, and decremented one count upon each detection of a non-frequent VES. Characterization of VES events continues regardless of the algorithm state. Counting of VES events occurs during the active state 200. When VES counter 60 reaches its programmed value (e.g., 50), the situation is analyzed as a failure of the therapy.

When the cardiac stimulation rate exceeds the maximum acceleration rate, e.g., 100 bpm, and when the VES counter 62 reaches its programmed value, then the algorithm is inactivated upon detection of the first frequent VES at state 300 (FIG. 4). Thus, the algorithm is inactivated upon detection of a frequent VES when the VEI interval cannot be shortened, after detection of a VES, without falling below its limit value, 500 ms in this instance, or when the cardiac stimulation rate is higher than the maximum acceleration rate (100 bpm) and the VES counter 62 reaches its programmed value (50).

The algorithm is activated at state 200 again when the simulation rate is lower than the maximum acceleration rate (100 bpm), and a new non-frequent VES is detected.

Figure 5:
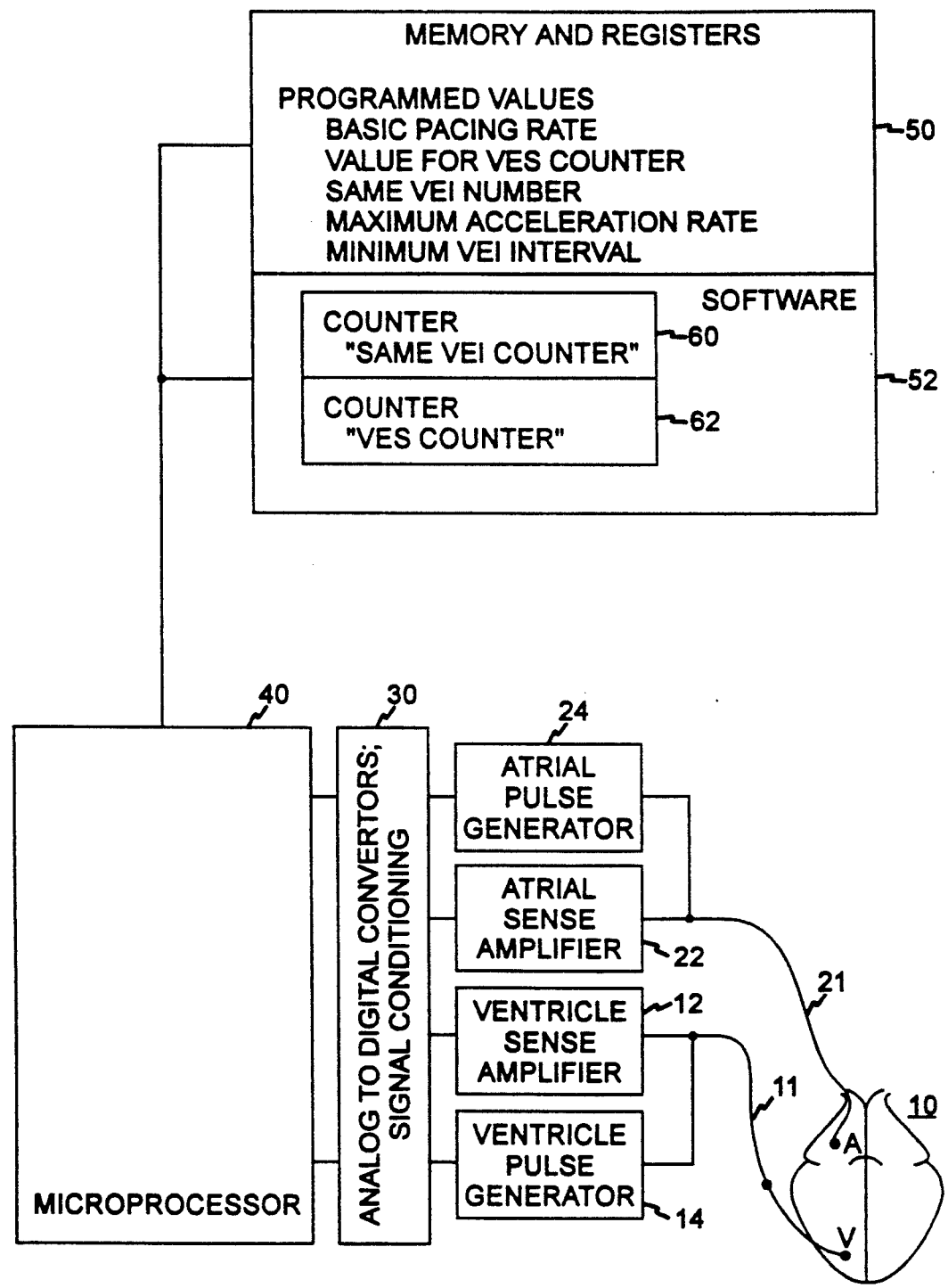
FIG. 5 is a block diagram of the apparatus of a preferred embodiment of the present invention.

As illustrated in FIG. 5, the detection of atrial and ventricular complexes and the measuring of the amplitude of these atrial and ventricular complexes are performed by conventional electronic means, e.g., digital microprocessor controlled devices having sense amplifiers, e.g., ventricle sense amplifier 12 and atrial sense amplifier 22 analog to digital conversion circuits 30 and microprocessor 40 with software 52 and suitable memory and registers for data processing and manipulalation. These devices also include an atrial pulse generator 24 and a ventricle pulse generator 14 for stimulating the atrium and ventricle under device control. The present invention is preferably implemented under software control, and occurs following acquisition of the cardiac electric signals by a conventional sense amplifier, e.g., by sensing electrical activity in the heart 10 atrium A and ventricle V using caridac leads 11 and 21, preferably after the acquired signals have been conditioned an converted to digital form in the usual manner. Accordingly, the parameters of the algorithm are programmable. Counters 60 and 62 are preferably implemented in and controlled by the software. Representative electronic circuits algorithm are those found in the series of pacemakers available from Ela Medical, Montrouge, France, offered under the CHORUS trademark. The method also could be performed using, and the apparatus constructed of, discrete circuitry, if desired.

One skilled in the art will appreciate that the present invention can be practiced by other than the described embodiments, which are presented for purposes of illustration and not of limitation.

We claim:

1. A method for controlling a cardiac pacemaker which detects the occurrence of spontaneous atrial and ventricular electrical activity and stimulates atrial and ventricular activity and includes a basic pacing rate, comprising the steps of:
   determining the occurrence of a ventricular extrasystole and whether it is a frequent or non-frequent ventricular extrasystole; and
   in response to the occurrence of a ventricular extrasystole applying a pacing control algorithm, including an atrial pacing rate and a ventricular pacing rate, comprising the following steps:
   stimulating the atrium,
   controlling the atrium at a faster pacing rate than the ventricle during a few cardiac cycles,
   synchronously controlling the ventricle during a period that is a multiple of a programmed number of cardiac cycles, and
   subsequent to each programmed number of cycles, slowing the ventricular pacing rate until one of the basic pacing rate is reached and a sinus event is detected.

2. The method of claim 1 wherein the pacing control algorithm step of stimulating the atrium further comprises:
   stimulating the atrium synchronous with the sensed ventricular extrasystole; and
   determining a ventricular escape interval VEI and a ventriculo-atrial interval VA based on the occurrence of the sensed ventricular extrasystole, the VA interval being shorter than the VEI interval.

3. The method of claim 2 wherein determining the VEI interval further comprises determining an average interval between two successive sinus events over a selected first number of cardiac cycles, and providing the VEI interval as a selected percentage of said determined average interval, the selected percentage being selected from among 50 and 100 percent.

4. The method of claim 3 wherein the selected percentage is on the order of 87.5 percent.

5. The method of claim 3 wherein the selected first number of cardiac cycles is on the order of 8.

6. The method of claim 2 wherein said synchronously controlling step further comprises selecting an atrio-ventricular delay interval AVD and, during said programmed number of cardiac cycles, maintaining the selected VEI interval constant, and, at each cycle, shortening the VA interval and lengthening the AVD interval while maintaining the equality:

$$VEI = VA + AVD.$$

7. The method of claim 6 wherein the programmed number of cardiac cycles is on the order of 20.

8. The method of claim 6 wherein said synchronously controlling step further comprises increasing the VEI interval subsequent to the occurrence of the programmed number of cardiac cycles and thereafter maintaining the VEI interval constant for the following programmed number of cardiac cycles.

9. The method of claim 8 wherein the programmed number of cardiac cycles is on the order of 20.

10. The method of claim 6 further comprising sensing the occurrence of a ventricular extrasystole that is a frequent ventricular extrasystole, and increasing the ventricular pacing rate by an increment corresponding to an acceleration slope in response to said frequent ventricular extrasystole.

11. The method of claim 10 further comprising:
   determining whether the accelerated ventricular pacing rate corresponds to a VEI interval that is lower that a predetermined duration corresponding to a selected high pacing rate; and
   inactivating the pacing control algorithm if the corresponding VEI interval is less than the predetermined pacing duration.

12. The method of claim 11 wherein inactivating the pacing control algorithm further comprises increasing the VEI interval by plateaus until the occurrence of one of the recovery of the basic pacing rate and a detected sinus event.

13. The method of claim 11 wherein the predetermined duration is on the order of 500 ms.

14. The method of claim 2 further comprising:
   maintaining a count of the programmed number of cardiac cycles on a counter and re-initializing the counter in response to each occurrence of a ventricular extrasystole; and
   inactivating the pacing control algorithm in response to one of the following:

sensing a ventricular extrasystole that is determined to be a frequent ventricular extrasystole and determining a VEI interval that is less than a predetermined duration corresponding to a first high pacing rate; and determining a pacing rate than is higher than a selected second high pacing rate after the counter reaches the programmed number of cardiac,. cycles.

15. The method of claim 14 wherein the predetermined duration is on the order of 500 ms and the second high pacing rate is on the order of 100 beats per minute.

16. The method of claim 14 further comprising reactivating the pacing control algorithm in response to sensing a ventricular extrasystole that is determined to be a non-frequent ventricular extrasystole and determining a VEI interval corresponding to a pacing rate that is less than the selected second high pacing rate.

17. The method of claim 16 wherein the predetermined duration is on the order of 500 ms and the second high pacing rate is on the order of 100 beats per minute.

18. The method of claim 1 further comprising maintaining a count of the programmed number of cardiac cycles on a counter and re-initializing the counter in response to the occurrence of a ventricular extrasystole.

19. The method of claim 1 further comprising, prior to applying the pacing control algorithm:
calculating an average interval between two successive sinus events for a selected second number of cardiac cycles;
determining whether a percentage of said calculated average interval exceeds a predetermined duration, said predetermined duration corresponding to a selected high pacing rate; and
applying the pacing control algorithm if the percentage exceeds the predetermined duration and not applying the pacing control algorithm if the percentage does not exceed the predetermined duration.

20. The method of claim 19 wherein the predetermined duration is on the order of 500 ms.

21. The method of claim 19 wherein the selected second number of cardiac cycles is on the order of 8.

22. The method of claim 1 wherein the programmed number of cycles is on the order of twenty and the multiple of the programmed number of cycles is the number of sensed frequent ventricular extrasystoles exceeding the number of sensed non-frequent extrasystoles by a number on the order of fifty.

23. Apparatus for controlling a cardiac pacemaker comprising:
means for monitoring atrial and ventricular electrical cardiac activity including detected and stimulated atrial and ventricular events and ventricular extrasystoles;
means for stimulating the atrium and the ventricle;
means for controlling the stimulating means for controllably stimulating separately the atrium and ventricle, said controlling means being responsive to the monitoring means and having a basic pacing rate; and
means for determining the occurrence of a ventricular extrasystole and identifying non-frequent and frequent ventricular extrasystoles;
wherein the controlling means responds to a sensed occurrence of a ventricular extrasystole by applying a pacing control algorithm including an atrial pacing rate and a ventricular pacing rate, and further comprising:
means for stimulating the atrium and controlling the atrium at a faster pacing rate than the ventricle during some cardiac cycles,
means for synchronously controlling the ventricle during a period that is a multiple of a programmed number of cardiac cycles, and subsequent to the programmed number of cycles, slowing the ventricular pacing rate until one of the basic pacing rate is reached and a sinus event is detected.

24. The apparatus of claim 23 wherein the controlling means stimulates the atrium synchronous with the sensed ventricular extrasystole, and further comprises means for determining a ventricular escape interval VEI and a ventriculo-atrial interval VA based on the occurrence of the sensed ventricular extrasystole, the VA interval being shorter than the VEI interval.

25. The apparatus of claim 24 further comprising means for determining an average interval between two successive sinus events over a selected first number of cardiac cycles, wherein the determining means determines the VEI interval to be a selected percentage of said determined average interval, the selected percentage being selected from among 50 and 100 percent.

26. The apparatus of claim 25 wherein the selected percentage is on the order of 87.5 percent.

27. The apparatus of claim 25, wherein the selected first number of cardiac cycles is on the order of 8.

28. The apparatus of claim 24 wherein said controlling means further comprises:
means for selecting an atrio-ventricular delay interval AVD and maintaining the duration of the VEI, VA, and AVD intervals according to the following equality:

$$VEI = VA + AVD,$$

and
means for maintaining the selected VEI interval constant during said programmed number of cardiac cycles and, at each cycle, shortening the VA interval and lengthening the AVD interval to maintain the equality.

29. The apparatus of claim 28 wherein the programmed number of cardiac cycles is on the order of 20.

30. The apparatus of claim 28 wherein said VEI determining means increases the VEI interval subsequent to the occurrence of the programmed number of cardiac cycles and thereafter maintains the VEI interval constant for the following programmed number of cardiac cycles.

31. The apparatus of claim 30 wherein the programmed number of cardiac cycles is on the order of 20.

32. The apparatus of claim 28 further comprising means for increasing the ventricular pacing rate by an increment corresponding to an acceleration slope in response to a sensed ventricular extrasystole that is identified as a frequent ventricular extrasystole.

33. The apparatus of claim 32 further comprising:
means for determining whether the accelerated ventricular pacing rate corresponds to a VEI interval that is lower that a predetermined duration corresponding to a selected high pacing rate, wherein said controlling means inactivates the pacing control algorithm if the corresponding VEI interval is less than the predetermined duration.

34. The apparatus of claim 32 wherein said controlling means inactivates the pacing control algorithm by increasing the VEI interval by plateaus until the occurrence of one of the recovery of the basic pacing rate and, a detected sinus event.

35. The apparatus of claim 33 wherein the predetermined duration is on the order of 500 ms.

36. The apparatus of claim 26 further comprising:
a counter for maintaining a count of the programmed number of cardiac cycles;
means for re-initializing the counter in response to each occurrence of a ventricular extrasystole; and
wherein the controlling means further comprises means for inactivating the pacing control algorithm in response to one of the following events:
a sensed ventricular extrasystole that is determined to be a frequent ventricular extrasystole and the determining means determines a VEI interval that is less than a predetermined duration corresponding to a first high pacing rate; and
a pacing rate that is higher than a selected second high pacing rate after the counter reaches the programmed number of cardiac cycles.

37. The apparatus of claim 36 wherein the predetermined duration is on the order of 500 ms and the second high pacing rate is on the order of 100 beats per minute.

38. The apparatus of claim 36 wherein the controlling means further comprises means for reactivating the pacing control algorithm in response to a sensed ventricular extrasystole that is determined to be a non-frequent ventricular extrasystole and a determined VEI interval corresponding to a pacing rate that is less than the selected second high pacing, rate.

39. The apparatus of claim 38 wherein the predetermined duration is on the order of 500 ms and the second high pacing rate is on the order of 100 beats per minute.

40. The apparatus of claim 23 further comprising a counter for maintaining a count of the programmed number of cardiac cycles, wherein the counter is re-initialized in response to the occurrence of a sensed ventricular extrasystole.

41. The apparatus of claim 23 wherein the controlling means further comprises:
means for calculating an average interval between two successive sinus events for a selected second number of cardiac cycles;
means for calculating a percentage of said calculated average interval following the occurrence of a ventricular extrasystole;
means for determining whether the determined percentage exceeds a predetermined duration, said predetermined duration corresponding to a selected high pacing rate; and
means for applying the pacing control algorithm if the calculated percentage exceeds the predetermined duration and for not applying the pacing control algorithm if the calculated percentage does not exceed the predetermined duration.

42. The apparatus of claim 41 wherein the predetermined duration is on the order of 500 ms.

43. The apparatus of claim 41 wherein the selected second number of cardiac cycles is on the order of 8.

44. The apparatus of claim 23 wherein the programmed number of cardiac cycles is on the order of twenty and the multiple of the programmed number of cycles is based on the number of sensed frequent ventricular extrasystoles exceeding the number of non-frequent ventricular extrasystoles by a number on the order of fifty.

* * * * *

UNITED STATES PATENT AND TRADEMARK OFFICE
CERTIFICATE OF CORRECTION

PATENT NO. : 5,312,451
DATED : May 17, 1994
INVENTOR(S) : Limousin, et al

It is certified that error appears in the above-indentified patent and that said Letters Patent is hereby corrected as shown below:

Title Page in the heading "[75] Inventors", after "Montrouge, all of" insert --France--;

Column 4, line 34, after "counter" insert -- 60 --;

Column 6, line 63, "60" should be --62--;

Column 7, line 20, before "microprocessor 40" insert --a--;

Column 7, line 21, "manipulalation" should be --manipulation--;

Column 7, line 29, "caridac" should be --cardiac--;

Column 7, line 35, "algorithm" should be deleted.

Signed and Sealed this

Twenty-ninth Day of November, 1994

Attest:

BRUCE LEHMAN

*Attesting Officer*      *Commissioner of Patents and Trademarks*